United States Patent
Mitelberg

(10) Patent No.: US 10,448,946 B2
(45) Date of Patent: *Oct. 22, 2019

(54) ENDOSCOPIC SUTURE CINCH

(71) Applicant: Apollo Endosurgery, Inc., Austin, TX (US)

(72) Inventor: Vladimir Mitelberg, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/374,206

(22) Filed: Dec. 9, 2016

(65) Prior Publication Data

US 2017/0086818 A1 Mar. 30, 2017

Related U.S. Application Data

(63) Continuation-in-part of application No. 14/206,098, filed on Mar. 12, 2014, now Pat. No. 9,788,831.
(Continued)

(51) Int. Cl.
*A61B 17/04* (2006.01)
*A61B 17/00* (2006.01)

(52) U.S. Cl.
CPC ...... *A61B 17/0487* (2013.01); *A61B 17/0467* (2013.01); *A61B 2017/0053* (2013.01);
(Continued)

(58) Field of Classification Search
CPC . A61B 17/0057; A61B 17/04; A61B 17/0406; A61B 17/0411; A61B 17/0412; A61B 17/046; A61B 17/0467; A61B 17/0469; A61B 17/0482; A61B 17/0487; A61B 17/08; A61B 17/083; A61B 17/10;
(Continued)

(56) References Cited

U.S. PATENT DOCUMENTS

| 5,026,379 A | 6/1991 | Yoon |
| 5,041,129 A | 8/1991 | Hayhurst et al. |

(Continued)

OTHER PUBLICATIONS

Contact. Dictionary.com Unabridged. Random House, Inc. Jul. 25, 2016. <Dictionary.com http:www.dictionary.com/browse/contact>.
Tubular. Dictionary.com. Dictionary.com Unabridged. Random House, Inc. http//www.dictionary.com/browse/tubular (accessed: Nov. 2, 2016).
(Continued)

*Primary Examiner* — Elizabeth Houston
*Assistant Examiner* — Kankindi Rwego
(74) *Attorney, Agent, or Firm* — Donald K. Jones

(57) ABSTRACT

A suture cinch, cinch applicator, and cinch loader for loading the cinch into the applicator are provided and permit re-use of the applicator with multiple cinches during an endoscopic procedure. The applicator can be loaded with a first cinch, apply the first cinch onto a portion of suture to fix the portion of suture relative to anatomical tissue, reloaded with a second cinch optionally using the loader, and subsequently used to apply the second cinch to fix another portion of suture to fix the other portion of suture relative to anatomical tissue. The cinch is a unitary tubular member through which the suture can be advanced when the cinch is loaded within the applicator. The cinch defines multiple ribs and a cutter in a wall thereof. Operation of the applicator deforms the ribs inward to retain the cinch on the suture and displaces the cutter to sever the suture.

20 Claims, 10 Drawing Sheets

Related U.S. Application Data

(60) Provisional application No. 61/777,607, filed on Mar. 12, 2013.

(52) U.S. Cl.
CPC .............. *A61B 2017/0417* (2013.01); *A61B 2017/0488* (2013.01)

(58) Field of Classification Search
CPC . A61B 17/105; A61B 17/122; A61B 17/1222; A61B 17/128; A61B 17/1285; A61B 2017/00575; A61B 2017/00579; A61B 2017/00601; A61B 2017/00606; A61B 2017/00619; A61B 2017/00623; A61B 2017/00628; A61B 2017/00632; A61B 2017/0403; A61B 2017/0404; A61B 2017/0406; A61B 2017/0417; A61B 2017/042; A61B 2017/0422; A61B 2017/0424; A61B 2017/0425; A61B 2017/0438; A61B 2017/0446; A61B 2017/0448; A61B 2017/0454; A61B 2017/0458; A61B 2017/0459; A61B 2017/0461; A61B 2017/0462; A61B 2017/0464; A61B 2017/0466; A61B 2017/047; A61B 2017/0495; A61B 2017/0496; A61B 1/018; A61B 2017/0419; A61F 2/2454; A61F 2/2457

See application file for complete search history.

(56) References Cited

U.S. PATENT DOCUMENTS

| | | |
|---|---|---|
| 5,141,520 A | 8/1992 | Goble et al. |
| 5,196,022 A | 3/1993 | Bilweis |
| 5,217,486 A | 6/1993 | Rice et al. |
| 5,304,185 A | 4/1994 | Taylor |
| 5,403,328 A | 4/1995 | Shallman |
| 5,433,725 A | 7/1995 | Christian et al. |
| 5,464,424 A | 11/1995 | O'Donnell, Jr. |
| 5,466,241 A | 11/1995 | Leroy et al. |
| 5,474,568 A | 12/1995 | Scott |
| 5,478,345 A | 12/1995 | Stone et al. |
| 5,514,159 A | 5/1996 | Matula et al. |
| 5,520,702 A | 5/1996 | Sauer et al. |
| 5,527,321 A | 6/1996 | Hinchliffe |
| 5,531,763 A | 7/1996 | Masti et al. |
| 5,545,180 A | 8/1996 | Le et al. |
| 5,573,496 A | 11/1996 | McPherson et al. |
| 5,584,860 A | 12/1996 | Goble et al. |
| 5,584,861 A | 12/1996 | Swain et al. |
| 5,601,557 A | 2/1997 | Hayhurst |
| 5,626,590 A | 5/1997 | Wilk |
| 5,626,614 A | 5/1997 | Hart |
| 5,643,320 A | 7/1997 | Lower et al. |
| 5,649,940 A | 7/1997 | Hart et al. |
| 5,653,717 A | 8/1997 | Ko et al. |
| 5,662,658 A | 9/1997 | Wenstrom, Jr. |
| 5,669,917 A | 9/1997 | Sauer et al. |
| 5,681,331 A | 10/1997 | de la Torre et al. |
| 5,685,823 A | 11/1997 | Ito et al. |
| 5,690,655 A | 11/1997 | Hart et al. |
| 5,720,766 A | 2/1998 | Zang et al. |
| 5,782,862 A | 7/1998 | Bonutti |
| 5,814,071 A | 9/1998 | McDevitt et al. |
| 5,887,594 A | 3/1999 | LoCicero, III |
| 5,944,739 A | 8/1999 | Zlock et al. |
| 5,964,764 A | 10/1999 | West, Jr. et al. |
| 5,993,467 A | 11/1999 | Yoon |
| 6,010,525 A | 1/2000 | Bonutti et al. |
| 6,036,699 A | 3/2000 | Andreas et al. |
| 6,068,648 A | 5/2000 | Cole et al. |
| 6,086,600 A | 7/2000 | Kortenbach |
| 6,086,608 A | 7/2000 | Ek et al. |
| RE36,974 E | 11/2000 | Bonutti |
| 6,159,234 A | 12/2000 | Bonutti et al. |
| 6,171,316 B1 | 1/2001 | Kovac et al. |
| 6,200,329 B1 | 3/2001 | Fung et al. |
| 6,224,614 B1 | 5/2001 | Yoon |
| 6,293,961 B2 | 9/2001 | Schwartz et al. |
| 6,312,448 B1 | 11/2001 | Bonutti |
| 6,475,230 B1 | 11/2002 | Bonutti et al. |
| 6,635,073 B2 | 10/2003 | Bonutti |
| 6,656,182 B1 | 12/2003 | Hayhurst |
| 6,663,639 B1 | 12/2003 | Laufer et al. |
| 6,663,641 B1 | 12/2003 | Kovac et al. |
| 6,695,852 B2 | 2/2004 | Gleason |
| 6,699,183 B1 | 3/2004 | Wimmer |
| 6,719,763 B2 | 4/2004 | Chung et al. |
| 6,719,764 B1 | 4/2004 | Gellman et al. |
| 6,733,509 B2 | 5/2004 | Nobles et al. |
| 6,755,843 B2 | 6/2004 | Chung et al. |
| 6,808,491 B2 | 10/2004 | Kortenbach et al. |
| 6,866,673 B2 | 3/2005 | Oren et al. |
| 6,921,361 B2 | 7/2005 | Suzuki et al. |
| 6,955,643 B2 | 10/2005 | Gellman et al. |
| 7,033,379 B2 | 4/2006 | Peterson |
| 7,048,755 B2 | 5/2006 | Bonutti et al. |
| 7,083,630 B2 | 8/2006 | DeVries et al. |
| 7,083,638 B2 | 8/2006 | Foerster |
| 7,087,012 B2 | 8/2006 | Ishibiki |
| 7,090,690 B2 | 8/2006 | Foerster et al. |
| 7,094,246 B2 | 8/2006 | Anderson et al. |
| 7,147,652 B2 | 12/2006 | Bonutti et al. |
| 7,150,757 B2 | 12/2006 | Fallin et al. |
| 7,153,314 B2 | 12/2006 | Laufer et al. |
| 7,179,277 B2 | 2/2007 | Cunningham |
| 7,198,599 B2 | 4/2007 | Goto et al. |
| 7,204,802 B2 | 4/2007 | De Leval |
| 7,220,266 B2 | 5/2007 | Gambale |
| 7,235,086 B2 | 6/2007 | Sauer et al. |
| 7,264,624 B2 | 9/2007 | Nash et al. |
| 7,318,802 B2 | 1/2008 | Suzuki et al. |
| 7,371,215 B2 | 5/2008 | Colliou et al. |
| 7,530,985 B2 | 5/2009 | Takemoto et al. |
| 7,601,161 B1 | 10/2009 | Nobles et al. |
| 7,703,459 B2 | 4/2010 | Saadat et al. |
| 7,727,144 B2 | 6/2010 | Suzuki |
| 7,775,973 B2 | 8/2010 | Okada et al. |
| 7,776,066 B2 | 8/2010 | Onuki et al. |
| 7,785,348 B2 | 8/2010 | Kuhns et al. |
| 7,918,867 B2 | 4/2011 | Dana et al. |
| 7,931,661 B2 | 4/2011 | Saadat et al. |
| 7,935,128 B2 | 5/2011 | Rioux et al. |
| 7,951,158 B2 | 5/2011 | Cantanese et al. |
| 7,988,656 B2 | 8/2011 | Uesugi et al. |
| 8,016,840 B2 | 9/2011 | Takemoto et al. |
| 8,021,376 B2 | 9/2011 | Takemoto et al. |
| 8,287,556 B2 | 10/2012 | Gilkey et al. |
| 8,308,765 B2 | 11/2012 | Saadat et al. |
| 9,788,831 B2 * | 10/2017 | Mitelberg .......... A61B 17/0487 |
| 2003/0109891 A1 | 6/2003 | Dana et al. |
| 2005/0240199 A1 | 10/2005 | Martinek et al. |
| 2006/0259044 A1 | 11/2006 | Onuki et al. |
| 2007/0270907 A1 | 11/2007 | Stokes et al. |
| 2008/0132944 A1 | 6/2008 | Kress |
| 2008/0234729 A1 | 9/2008 | Page et al. |
| 2009/0216308 A1 | 8/2009 | Hartley |
| 2009/0312775 A1 | 12/2009 | Gilkey et al. |
| 2011/0301619 A1 | 12/2011 | Walters |
| 2012/0157765 A1 | 6/2012 | Mitelberg |
| 2012/0158023 A1 | 6/2012 | Mitelberg et al. |
| 2012/0271327 A1 | 10/2012 | West |

OTHER PUBLICATIONS

Rib. Dictionary.com. Dictionary.com Unabridged. Random House, Inc. http//www.dictionary.com/browse/rib (accessed: Nov. 2, 2016).

* cited by examiner

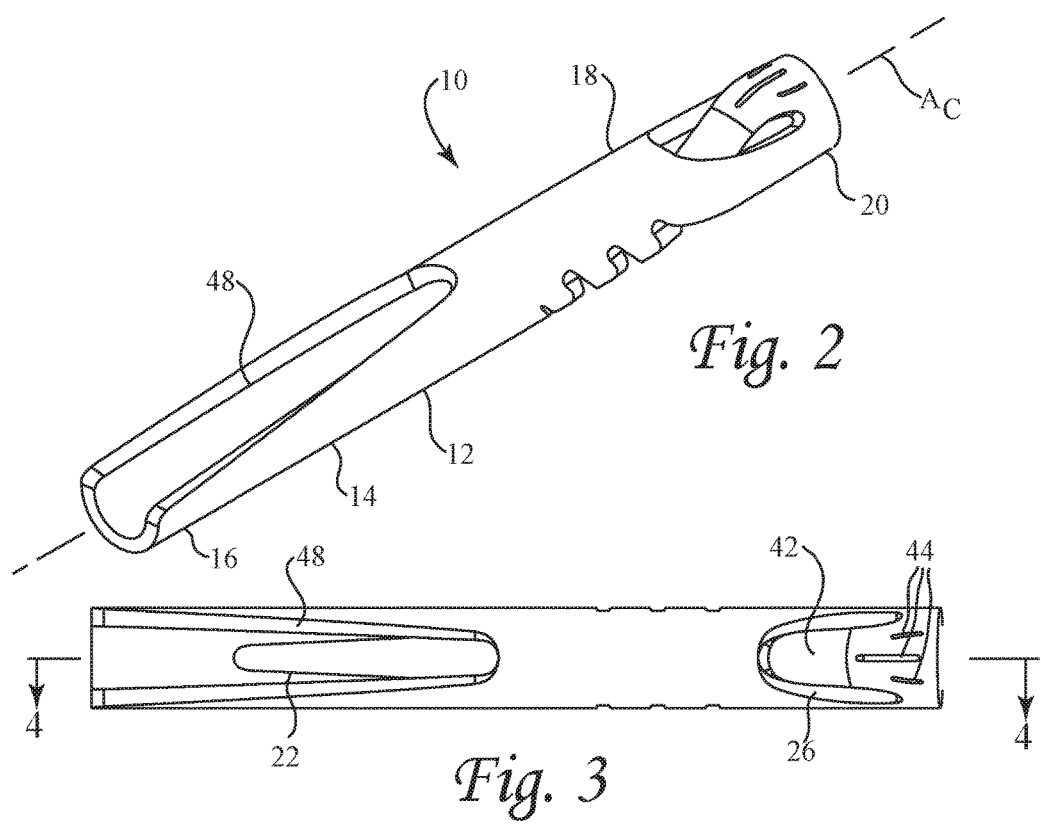
Fig. 2
Fig. 3
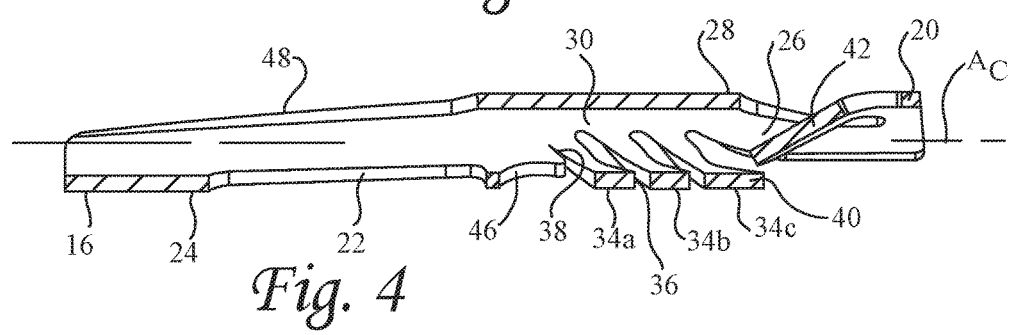
Fig. 4
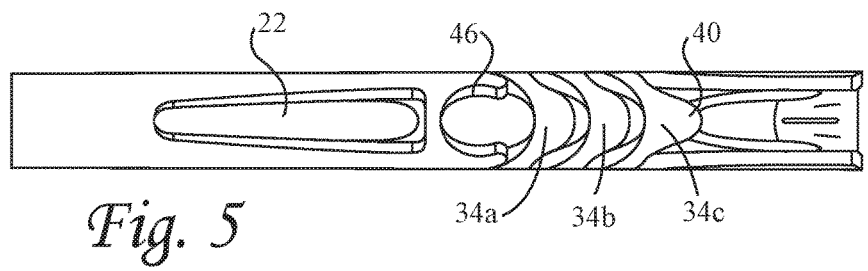
Fig. 5

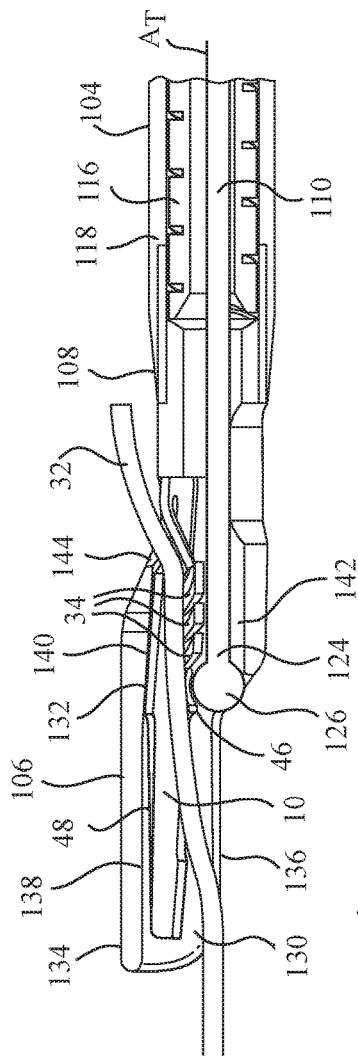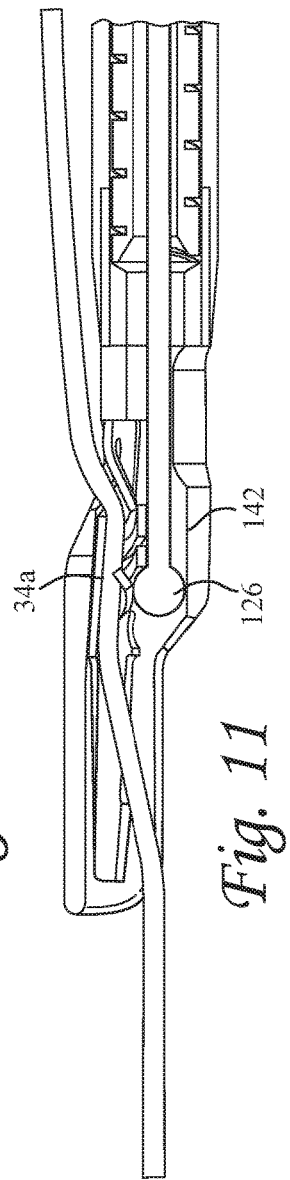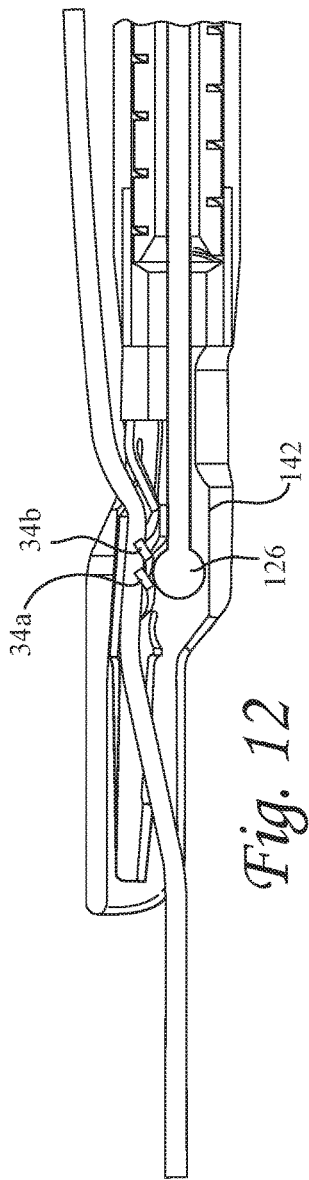

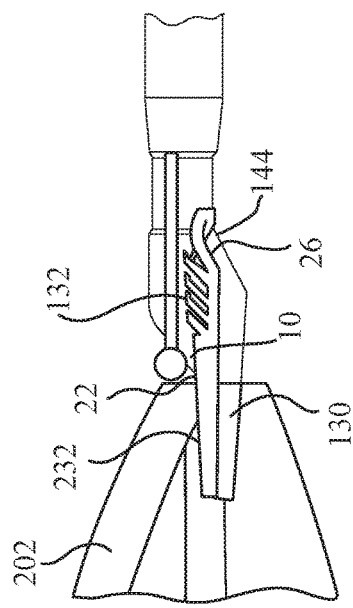
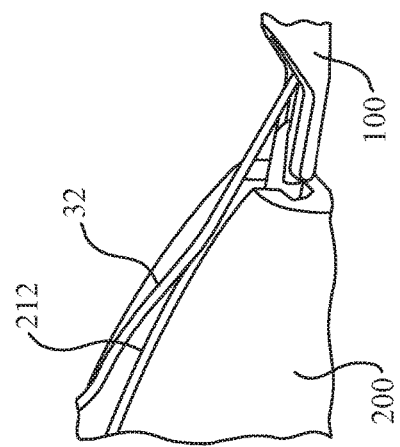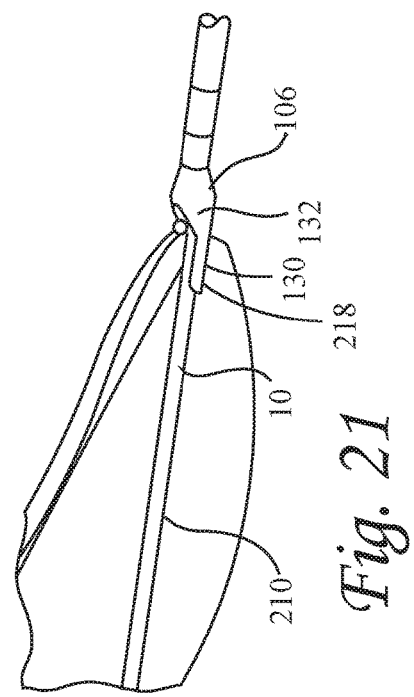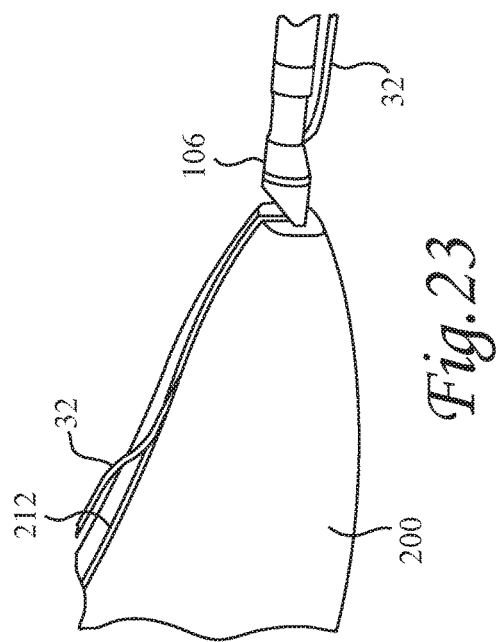

ENDOSCOPIC SUTURE CINCH

CROSS-REFERENCE TO RELATED APPLICATIONS

This application is a continuation-in-part of U.S. Ser. No. 14/206,098, filed Mar. 12, 2014, which claims benefit of U.S. Provisional App. No. 61/777,607, filed Mar. 12, 2013, which are hereby incorporated by reference herein in their entireties.

BACKGROUND OF THE INVENTION

Field of the Invention

The present invention relates to a device that can be inserted into a body through a natural orifice with an endoscope or other steerable guide member. The present invention may be used in conjunction with a suturing instrument to secure an applied suture to the tissue of a mammal, whether human or not, and whether or not alive.

State of the Art

Natural orifice surgery involves passing surgical instruments in association with an endoscopic camera through a natural orifice, such as the mouth, vagina, or anus, to a desired organ. By avoiding major incisions through the skin, muscle, and nerves of the abdomen, patients may experience a quicker recovery with less pain and scarring while further reducing the post-operative risk of surgery.

In co-owned US Pub. Nos. 20090312775A1 and 20120157765, endoscopic suturing devices suitable for use in a natural orifice procedure are described. The devices described each have a structure with a sufficiently small distal profile for delivery through a natural orifice, while providing a needle movable on an arm through a large opening and closing angle and which produces a large force upon the needle for piercing tissue to perform a surgical operation such as tissue approximation and suturing. A length of suture is permanently attached to the needle and forms stitches about tissue engaged at the distal end of the device as the needle is moved through the tissue and the distal end of the device is moved relative to the tissue. After one or more stitches have been formed in the tissue, the needle is released from the device and the free end of the suture is secured relative to the tissue. In accord with one manner of securing the free end of the suture, portions of the suture may be tied together about the tissue. In accord with another manner of securing the suture, a cinch element is advanced over the suture and cinches the tissue between the needle on one side of the tissue and the cinch on the other side of the tissue.

In addition to the cinch and cinch-applying instrument described in the above-referenced publication, other cinch instruments and deployable cinches are known. For example, referring to prior art FIG. 1, also known is a cinch applicator 910 for use in deploying the two parts 912, 914 of a cinch onto suture 916 in a surgical procedure. The applicator 910 includes an elongate flexible tubular member 918, a hypotube 920 fixed to the distal end 922 of the flexible tubular member 918, a flexible shaft 924 extending through the tubular member 918 and the hypotube 920, and a proximal handle (not shown) for moving the shaft 924 longitudinally relative to the tubular member 918. The hypotube 920 defines a distal housing 926 and a proximal lateral window 928. A slidable plunger 930 formed with a guillotine 932 is provided within the hypotube 920, with the guillotine 932 fully proximal of the housing 926 and distal of the lateral window 928.

The two-part cinch includes a collar 912, and a plug 914 engageable within the collar. The collar 912 has a cylindrical outer shape that is retained in the distal housing 926 of the hypotube 920 with a simple dimpling mating structure. The collar 912 also includes a proximal inner lip 933, and an outer lip 934 seating at the distal end of the hypotube 920 and having a flat distal facing end 935. The plug 914 of the cinch is attached to the distal end of the flexible shaft 924. The plug 914 has an enlarged distal flange 936 corresponding in size and shape to the outer lip 934 on the collar 912. The plug 914 has an elongate tubular body 938 defining a throughbore 940 in which the flexible shaft 924 extends, and a proximal circumferential exterior groove 942. A distal portion of the shaft 924 has a bend 944 to facilitate retention within the throughbore 940. The distal end of the shaft 924 has a rounded bead 946 that sits at the flange 936 of the plug. The bend 944 and the bead 946 trap the flexible shaft relative to the plug.

In operation, from outside the patient, the proximal end of the suture 916 is thread through the collar 912 and hypotube 920 and out of the lateral window 928. Then the applicator 910 is advanced through an endoscope so that the elements of the cinch are provided adjacent the stitched tissue. When the handle is operated, the shaft 924 is retracted to draw the plug 914 into an interference fit within the collar 912, with the inner lip 933 of the collar positively engaging the outer groove 942 on the plug. The suture 916 is captured between the outer surface of the plug 914 and the inner surface of the collar 912 so that the cinch is secured to the suture. Upon further retraction of the shaft 924, the shaft is pulled such that the bend 944 and bead 946 of the shaft 924 are pulled all the way through the plug 914 until released therefrom, and drawn back into engagement with the plunger 930. As the shaft 924 is moved further proximally relative to the hypotube 920, movement of the shaft 924 causes the guillotine 932 to slide past the window 928 and sever the proximal portion of the suture 916 from the portion of the suture attached to the cinch. Once the suture 916 is severed, a jerking motion is applied to the applicator 910 to release the engagement formed by the dimpling structure between to the cinch 912, 914 and applicator 910.

The applicator and cinch are thereby together capable of effectively securing stitched suture to tissue. Once the cinch 912, 914 is secured to the suture, the applicator 910 is no longer capable of securing another cinch on another area of suture, as the bend 944 and bead 946 of the shaft 924 cannot be inserted through another plug during the procedure; the shaft is intended to be proximally loaded through the plug. Thus, the applicator is a single-use device.

SUMMARY OF THE INVENTION

In accord with the invention, a suture cinch, cinch applicator, and cinch loader for loading the cinch into the cinch applicator are provided and permit re-use of the applicator with multiple suture cinches during an endoscopic surgical procedure. The cinch applicator can be loaded with a first cinch, apply the first cinch onto a portion of suture to fix the portion of suture relative to anatomical tissue, reloaded with a second cinch using the loader, and subsequently used to apply the second cinch to fix another portion of suture to fix the other portion of suture relative to anatomical tissue. The process can be repeated to apply additional cinches on suture as required during a procedure.

The cinch is a tubular member having a periphery, a longitudinal axis, a first portion defining a first end of the tubular member, and a second portion longitudinally opposite the first portion defining a second end of the tubular member. An entry opening is provided in a first side of the periphery at the first portion, and an exit opening is provided in a second side of the periphery at the second portion, with the first and second sides being located on opposing sides of the periphery such that the entry and exit openings face in opposite directions. A suture pathway extends from the entry opening to the exit opening. At least one plastically deformable rib extends partially about the periphery of the tubular member transverse to the longitudinal axis. A seat is provided in the first side of the periphery between the entry opening and the rib for receiving a force-applying member of the applicator, discussed below. The cinch may optionally define a deformable cutter. In preferred embodiments, the cinch is of the generally small size required to accommodate securing a single strand of suture dimensioned for securing two portions of soft tissue together.

The applicator includes a handle having first and second relatively displaceable handle members. An elongate flexible tubular member is coupled to the first handle member, and a rigid cinch housing for retaining the cinch during use is fixed at the distal end of the tubular member. A flexible shaft is coupled to the second handle member, and terminates in a force-applying member, preferably in the form of a bead.

According to a preferred embodiment, the cinch housing includes a socket in which the cinch is received. The distal end of the housing is partially tubular, providing lateral access to the entry opening in the cinch, and has a support wall for the cinch that preferably extends parallel to the longitudinal axis of the tubular member. A central portion of the socket tapers in diameter in a distal to proximal direction. When the cinch is seated in the socket, the force-applying member is seated in the seat of the cinch and slight retraction on the shaft operates to retain the cinch in the housing. However, the bead cannot be readily further retracted, as the housing tapers in diameter and the ribs block passage of the bead. The proximal portion of the housing includes a window for alignment with the exit opening of the cinch and through which suture may be passed.

With the handle in a first position, the bead is located distal of said distal opening of the cinch housing allowing loading of a cinch into the socket of the housing. When the handle is in a second position, the bead engages within the seat of the cinch and enters the socket to retain the cinch in the housing. In accord with the invention, when a sufficient force is applied at the handle to move the handle from the second position into a third position, the bead is forcibly drawn along the cinch against the ribs of the cinch to sequentially deform the ribs of the cinch against the suture and onto the suture and thereby lock the cinch onto the suture.

In accord with another aspect to the invention, the cinch includes an integral tab that extends at an oblique angle relative to the longitudinal axis of the cinch to define a guide that deflects suture advanced through the tubular member toward and through the exit opening.

In accord with a further aspect of the invention, the cinch includes an integral tab that is deformed by movement of the bead along the cinch to deform the tab against the suture extending within the pathway to cut the suture. The tab that deflects suture is preferably the same tab that cuts the suture.

Also in accord with the invention, the cinch is a unitary single-part device, preferably constructed from a metal hypotube, and which is laser cut to define the entry and exit openings, the ribs, and the suture deflecting, suture cutting tab.

In accord with another preferred aspect of the invention, the cinch is loaded within the cinch housing such that the ribs are oriented at an oblique angle relative to the longitudinal axis of the tubular member, and consequently at an oblique angle relative to the displacement axis of the shaft. Therefore, when the handle is operated to move the bead from the first position to the third position, the bead is proximally retracted in a linear manner, but an angle and relative to the ribs. This facilitates deformation of the ribs against the suture. Where the cinch defines a suture cutter, as the bead is drawn proximally along the cinch, the bead displaces the suture cutter to cause it to cut the suture.

In accord with another aspect of the invention, in an embodiment in which the cinch does not define an integrated cutter, the cinch applicator is provided with suitable means to cut the suture after the cinch is secured on the suture. By way of example only, such means includes a cutter that can be moved relative to the window in the housing in a relatively longitudinal or rotational manner, or a punch that is sufficiently movable through the window to sever the suture extending through the window from the suture attached to the cinch and tissue. Once the shaft is fully retracted into the third position by operation of the handle and the suture is cut, the bead is located proximal of the ribs and any suture deflecting/cutter tab, thereby allowing retraction of the entire applicator relative to cinch and release of the cinch from the cinch housing. The applicator is then withdrawn from the body of the patient.

In accord with another aspect of the invention, a loader is provided to load a suture cinch into the applicator. This is advantageous as the cinch is particularly small, thereby rendering it somewhat impractical for manipulation into the proper orientation into the housing by the fingers of an operator. The loader can be provided preloaded with a cinch or can be operator-loaded with a cinch, as the operation is easier than loading the housing. The loader includes a cinch recess in which to receive the cinch, and a cinch pusher displaceable relative to the recess. The distal end of the pusher has a tip with a first portion shaped to engage the lateral entry opening in the cinch to retain the cinch, and a second portion that butts against the first end of the cinch such that it can apply a pushing force thereagainst. The proximal end of the recess is enlarged in size and shaped to accommodate receiving the distal end of the cinch housing. When the housing is pushed in the enlarged proximal recess, the pusher is activated to load the cinch into the socket. The loader also includes a suture guide slot to facilitate guiding suture into the lateral entry opening of the cinch after the cinch is loaded into the socket.

The described system has particular use in endoscopic procedures in a NOTES procedure in which an endoscopic stitching instrument has applied one or more stitches of suture through tissue, in a procedure on gastrointestinal tissue where it is necessary or desirable to secure one or more a sutures, or in any other endoscopic procedure where it is necessary or desirable to secure one or more sutures. In a mode of such stitching, a needle fixed to one of the suture is advanced through the tissue and carries the suture through the tissue. Once the tissue is sufficiently stitched to approximate the tissue, the cinch applicator with cinch is provided for cinching the suture against the tissue and/or relative to the suture needle. Subsequently, the cinch applicator may be withdrawn from the patient, a new cinch may be loaded into the cinch housing, preferably through use of the cinch loader, and the cinch applicator can be used again to secure an addition suture. The process may be repeated as necessary.

Additional objects and advantages of the invention will become apparent to those skilled in the art upon reference to the detailed description taken in conjunction with the provided figures.

BRIEF DESCRIPTION OF THE DRAWINGS

FIG. 2 is a perspective view of a first embodiment of a suture cinch according to the invention.

FIG. 3 is a first side view of the suture cinch.

FIG. 4 is a longitudinal section view of the suture cinch taken across line 4-4 in FIG. 3.

FIG. 5 is a second side view of the suture cinch.

FIG. 10 is a longitudinal section view of the distal end of the cinch applicator loaded with a cinch.

FIGS. 11 and 12 are views similar to FIG. 10, with the bead of the cinch applicator shown displaced across the ribs of the cinch.

FIG. 21 is a partially transparent perspective view of the distal end of the cinch applicator coupled to the cinch loader.

FIG. 22 is a transparent side elevation view of the distal end of the cinch applicator coupled to the cinch loader, illustrating loading of a cinch into the cinch housing.

FIG. 23 is a perspective view of the distal end of the cinch applicator coupled to the cinch loader, illustrating advancing suture through the cinch loader and into the cinch applicator.

FIG. 24 is a perspective view of the distal end of the cinch applicator coupled to the cinch loader, illustrating removal of the suture relative to the cinch loader.

DETAILED DESCRIPTION OF THE PREFERRED EMBODIMENTS

In accord with the invention, a suture cinch 10 (FIGS. 2 through 8), a cinch applicator 100 (FIGS. 9 through 17), and cinch loader 200 for loading the cinch 10 into the cinch applicator 100 (FIGS. 18 through 24) are provided and permit re-use of the applicator with multiple suture cinches during an endoscopic surgical procedure.

In accord with a method of the invention, described further below, the cinch applicator can be loaded with a first cinch, apply the first cinch onto a portion of suture to fix the portion of suture relative to anatomical tissue, reloaded with a second cinch, and subsequently used to apply the second cinch to fix another portion of suture to fix the other portion of suture relative to anatomical tissue. Loading and reloading of the applicator with cinches is facilitated with the cinch loader. The process can be repeated to apply additional cinches on suture as required during a procedure.

Figure 6:
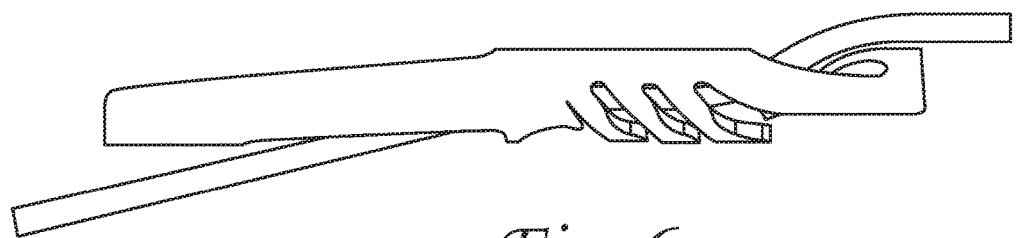
FIG. 6 is a side elevation view of the suture cinch with the cinch in the same orientation as FIG. 4, with suture extending through the cinch.
Figure 7:
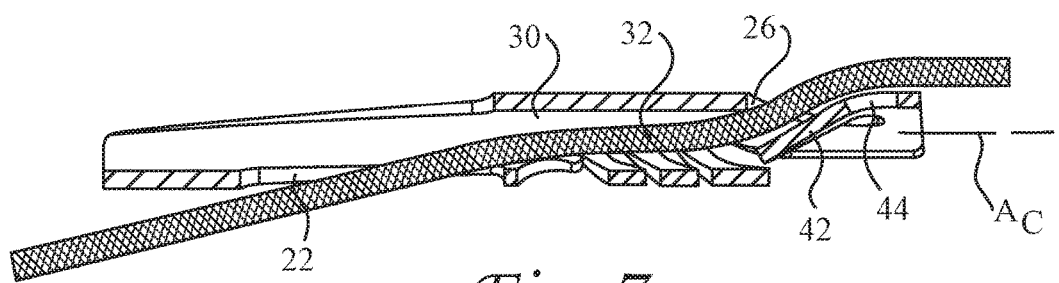
FIG. 7 is a view similar to FIG. 4, with suture extending through the cinch.

Turning now to FIGS. 2 through 5, the cinch 10 is a unitary tubular element preferably formed from a portion of a metal hypotube, such as a stainless steel tube, and is preferably laser cut to define the features thereof in a unitary construct. Alternatively, the tubular element can made from a plastic, including a bioresorbable material, and can also be machined or molded to define the features thereof, as now described. The tubular element has a round periphery 12 defining a circumference, a longitudinal central axis $A_L$, a first portion 14 defining a first end 16 of the tubular element, and a second portion 18 longitudinally opposite the first portion and defining a second end 20 of the tubular element. An elongate entry opening 22 is provided in a first lateral (hemi-tubular) side 24 of a periphery 12 (i.e., extending a first 180° about the axis $A_C$) at the first portion 14, and an exit opening 26 is provided in a second lateral (hemi-tubular) side 28 of the periphery (i.e., extending an opposite second 180° about the axis $A_C$) at the second portion 18, with the first and second hemi-tubular sides 24, 28 being located on opposing sides of the periphery 12 such that the entry and exit openings 22, 26 face in opposite directions. The entry opening 22 preferably expands in lateral dimension in a direction defined from the first end toward the second end. A suture pathway 30 extends from the entry opening 22 to the exit opening 26, generally parallel to the longitudinal axis $A_L$. Referring to FIGS. 6 and 7, the cinch 10 and pathway 30 are of the generally small size required to accommodate receiving and securing a single strand of suture 32 dimensioned for coupling two portions of soft tissue together. By way of example only, the cinch 10 has a length of 4 to 15 mm and a maximum diameter of 0.5 to 1.5 mm.

Referring back to FIGS. 4 and 5, at least one plastically deformable rib, collectively 34 (with three ribs 34a, 34b, 34c shown in the illustrated embodiment), is provided along the first side 24 of the second portion 18 of the tubular element and extends partially about the periphery of the tubular element to the longitudinal axis $A_C$. The ribs 34 are formed and separated by preferably laser cut slots that extend into the tubular element at an oblique angle relative to the longitudinal axis, such that the ribs 34 are also oriented at a like angle. As a result, each of the ribs 34 has a leading end 36 oriented toward the second end 20 of the tubular element, and a trailing end 38 angled back toward the first end 16 of the tubular element; i.e., the ribs are obliquely angled relative to the axis $A_C$ from the first end 16 toward the second end 20. The slot is formed such that the leading end is defined by a curvilinear cut and the trailing end is defined by a straight cut. This results in a defined weakness in the rib 34 such that the rib has a tendency to fold over into securement with suture when subject to a force, as described below. That is, the ribs 34 are formed such that when subject to the force of the applicator as described below, the ribs will twist and extend transversely into the suture pathway. The last of the ribs preferably includes a tongue-like projection 40.

Figure 8:
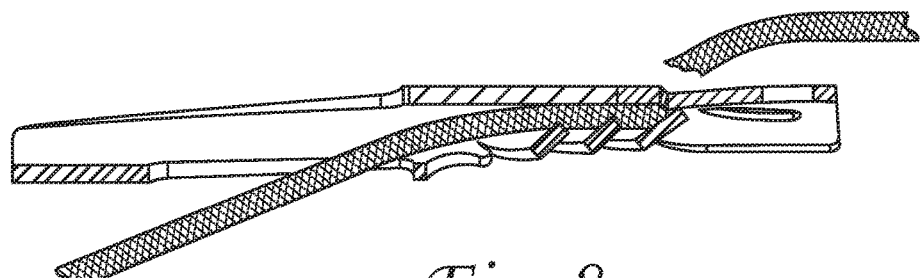
FIG. 8 is view similar to FIG. 7, but with the cutter tab displaced to cut suture extending through the exit opening.

Referring to FIGS. 3, 4, and 7, an optional tab 42 is defined at the exit opening 26, extending from adjacent the second end 20 at the second side 24 of the second portion 18 of the tubular element and deflected radially inward into the interior of the tubular element. The tab 42 is adapted to deflect and guide suture 32 advanced through the pathway 30 (from the entry opening 22) toward said exit hole 26. The tab 42 is provided with several longitudinal slits 44 to reduce its bending stiffness. As described in more detail below, the tab 42 is adapted to be bent by the tongue-like projection 40 on the last rib 34*c* and displaced toward the exit hole 26 by operation of the applicator, such that it cuts suture extending between the pathway 30 and exit hole 26, as shown in FIG. 8.

Referring to FIGS. 4 and 5, an opening in the first side of the tubular element between the entry opening 26 and the ribs 34 defines a seat 46 for receiving a force-applying member of the applicator. The seat 46 preferably has a generally horseshoe-shape, formed opposite of a first 34*a* of the ribs.

Figure 1:
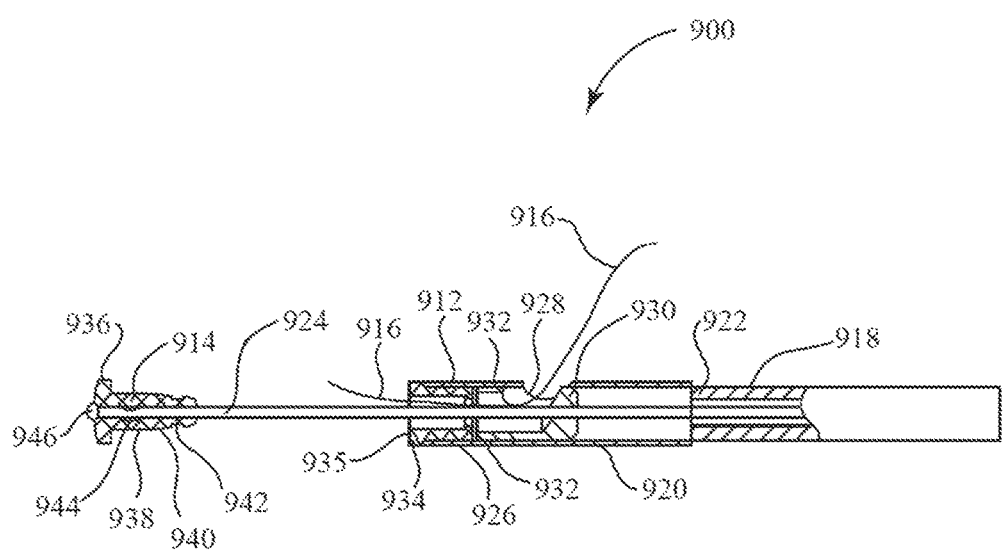
FIG. 1 is a partial section of a distal end of a prior art endoscopic cinch applicator and a prior art two-part cinch.

Referring to FIGS. 1 through 3, the first side 24 of the tubular element is preferably substantially straight from the first end 16 to the second end 20. The second side 26 of the first portion 14 of the cinch, from the first end 16 and along the length of the entry opening 22, is canted relative to the second side of the second portion 18. This is preferably structured by cutting into the periphery of the second side of the first portion at 48 along an oblique angle relative to the longitudinal axis to open the periphery thereat. The oblique angle of the cut is preferably 9° to 11°. As discussed below, this shape facilitates providing the cinch in a preferred orientation within the applicator such it the applicator can apply an optimal deformation force to deform the ribs and cutter tab.

With reference to the following description of the applicator, the terms "proximal" and "distal" are defined in reference to the hand of a user of the device, with the term "proximal" being closer to the user's hand and generally at a 'handle' end of an instrument, and the term "distal" being further from the user's hand, and generally at an operative end of an instrument such as to often be located further within a body of the patient during use.

Figure 9:
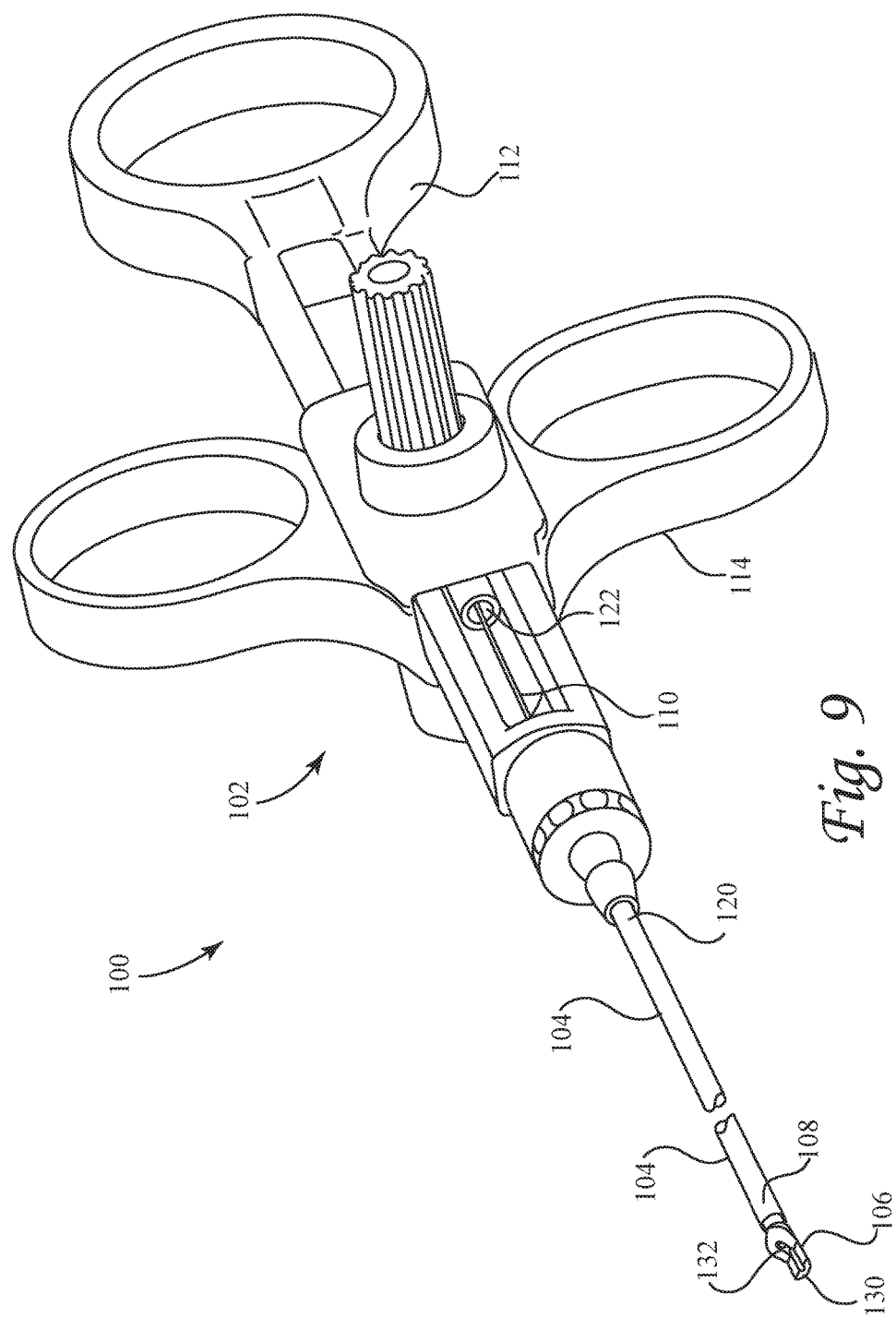
FIG. 9 is a perspective view of the cinch applicator.

Turning now FIG. 9, the applicator 100 includes a proximal handle 102, a flexible tubular member 104, a rigid cinch housing 106 located at the distal end 108 of the tubular member and adapted for retaining the cinch 10 during use of the applicator, and a flexible shaft 110. The proximal handle 102 has first and second relatively displaceable handle members 112, 114 for moving the shaft 110 relative to the cinch housing 106.

Referring to FIG. 10, the flexible tubular member 104 has a longitudinal axis along which the shaft 110 extends, and comprises a preferably flat wound coil 116 surrounded by a lubricious polymer sheath 118. The flexible tubular member 110 preferably has a sufficiently small diameter and sufficient length to extend completely through the working channel of an endoscope, but may be used outside the endoscope. Suitable dimensions for use within a working channel of an endoscope include an outer diameter of 2.0 to 2.2 mm and a length of 190 to 300 cm. In addition, the tubular member 110 is sufficiently flexible to advanced through a tortuous path; i.e., to extend through the working channel of a retroflexed endoscope—one that is bent through an arc of 180°. The tubular member 110 includes a proximal end 120 coupled to the first handle member 112.

The flexible shaft 110 includes a proximal end 122 coupled to the second handle member 114, and a distal end 124 terminating in a bead 126, preferably in the form of a sphere. The bead 126 is preferably unitarily integrated at the distal end of the shaft. The bead 126 can take alternative forms from spherical including, but not limited to, oblong and pyramidal. In all forms, the bead 126 preferably tapers toward its proximal end where it joins to or is otherwise coupled to the distal end 124 of the shaft 110. Further, the bead 126 may comprise a discrete structure from the shaft. Whether unitary with or discrete therefrom, the bead may be coupled to the distal end of the shaft by any suitable means including, by way of example, solder, braze, or a bonding agent, a pin, or an articulating link.

According to a preferred embodiment, the cinch housing 106 is crimped, welded, or otherwise fixed to the distal end 108 of the tubular member 104. The cinch housing 106 defines a distal longitudinal hood 130 and a central socket 132 in which the cinch 10 is received. The hood 130 partially surrounds the cinch 10, protecting the distal portion 14 of the cinch from the tissue during use. The hood 130 has a curved first surface 134 and a flat second surface 136. The flat surface 136 defines a groove 138 that co-extends into the socket 132. The groove 138 is laterally open, thereby providing lateral access to the entry opening 22 of the cinch 10. The groove 138 preferably extends parallel to the longitudinal axis $A_T$ of the tubular member 104 for support of the angled second side (at cutout 48) of the first portion 14 of the cinch 10. The socket 132 tapers in diameter in a distal-to-proximal direction. The taper of the socket is preferably defined by a canted wall 140 extending proximally from the hood 130 and oriented obliquely relatively to the longitudinal axis $A_T$ of the tubular member 104 and an opposing axial wall 142 oriented parallel to the longitudinal axis of the tubular member. The canted wall 140 and axial wall 142 are preferably angled at approximately 9° to 11° relative to each other. The proximal portion of the housing includes a window 144 that aligns with the exit opening 126 of a loaded cinch 10 and through which suture 32 may be passed. The cinch housing 106 preferably has a maximum length of 25 mm and a maximum outer diameter of 2.6 mm such that it can be advanced through a 2.8 to 3.2 mm working channel of an endoscope.

Referring to FIGS. 9 and 10, with the handle 102 in a first position (e.g., with the second handle member 114 in its most distal location relative to the first handle member 112), the bead 126 is located distal of the socket 132 of the cinch housing allowing loading of a cinch 10 into the socket of the housing. The cinch 10 is loaded such that the ribs 34 sit at an oblique angle relative to the axial wall 142, and consequently at an oblique angle relative to the displacement axis of the shaft 110 once the shaft is drawn into retraction parallel to the longitudinal axis $A_T$ of the tubular member 110.

Then, when the handle 102 is in a second position (with the second handle member is in a relatively proximal location relative to the first position), the bead 126 engages within the seat 46 of the cinch and at least partially enters the socket 132 to retain the cinch 10 in the housing 106 (the configuration specifically shown in FIG. 10). The shaft 110 with bead 126 cannot be readily further retracted, as the space between the axial wall 142 of the socket 132 and the ribs 34 of the cinch 10 is too small, and blocks passage of the bead.

In either the first or second handle positions, the suture 32 can be advanced into the entry opening 22, through the pathway 30, and out the exit opening 26 of the cinch, and out the window 144 of the housing. Once the suture 32 is thread through the cinch (and therefore extends within the socket) and out of the window, the applicator is advanced into the patient. This is preferably done through whatever path the suture was retrieved through, including the working channel of an endoscope or outside an endoscope. The applicator is advanced until the hood contacts the tissue, the suture is tensioned, and then the handle is operated to secure the cinch on the suture as follows.

Figure 13:
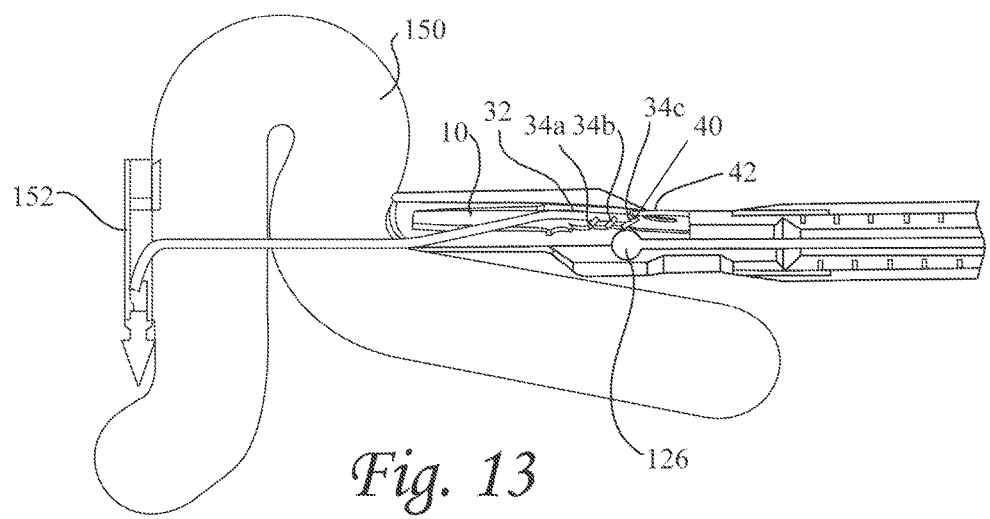
FIG. 13 is a longitudinal section view showing final cinching of the cinch onto suture at tissue.
Figure 14:
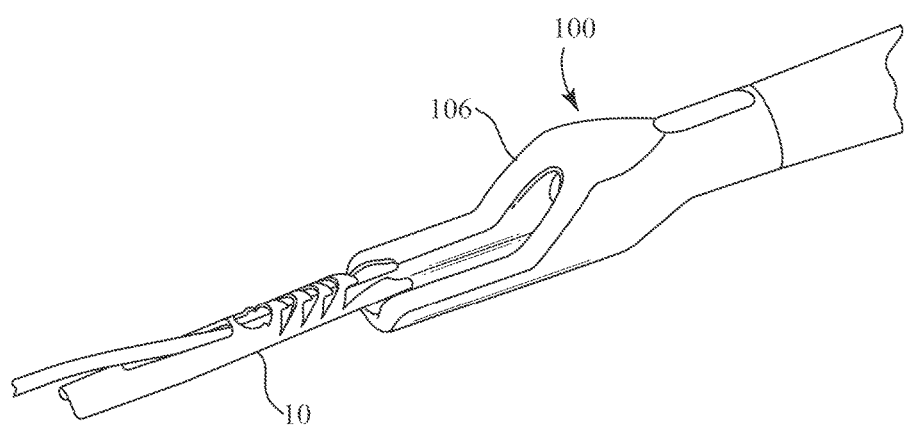
FIG. 14 is a broken distal end perspective view illustrating release of the cinch from the cinch applicator.

In accord with the invention, when a sufficient force is applied at the handle to move the handle from the second position into a third position (with the second handle member in a relatively proximal location relative the second position), the bead 126 is drawn proximally into the space between the axial wall 142 and the ribs 34. As noted above, this space is too small to receive the bead 126. However, as shown in FIGS. 11, 12 and 13, the ribs 34a, 34b, 34c are adapted in structure to sequentially deform into the pathway 30 of the cinch under a defined force so as to securely contact the suture 32 and thereby lock the cinch onto the suture. To facilitate application of the force, the axial wall 142 is positioned and oriented to guide the bead 126 linearly and axially relative to the longitudinally axis $A_T$ of the tubular member as the second handle member 114 is moved relatively proximal toward the first handle member 112 into the third position. However, this linear retraction is at an angle relative to the ribs 34. This results in the bead 126 applying a deformation force against the ribs 34 that increases with each proximally subsequent rib (increasing from rib 34a to rib 34b to rib 34c). Referring to FIG. 13, where the cinch 10 defines a suture cutter tab 42, as the bead 126 is drawn proximally along the cinch, the bead 126 displaces the suture cutter tab 42 to cause it to cut the suture. This is preferably caused by the tongue-like projection 40 on deformed rib 34c contacting the cutter tab 42 to effect the displacement. Referring to FIGS. 13, and 14, after the cutter tab 42 has severed the suture 32, the applicator 100, and thus housing 106, may be retracted relative to the tissue 150 and any other structure (such as a suture tag or releasable suture needle 152) securing another portion of the suture within the tissue, and the cinch is thereby released from the housing 106 of the applicator.

Figure 15:
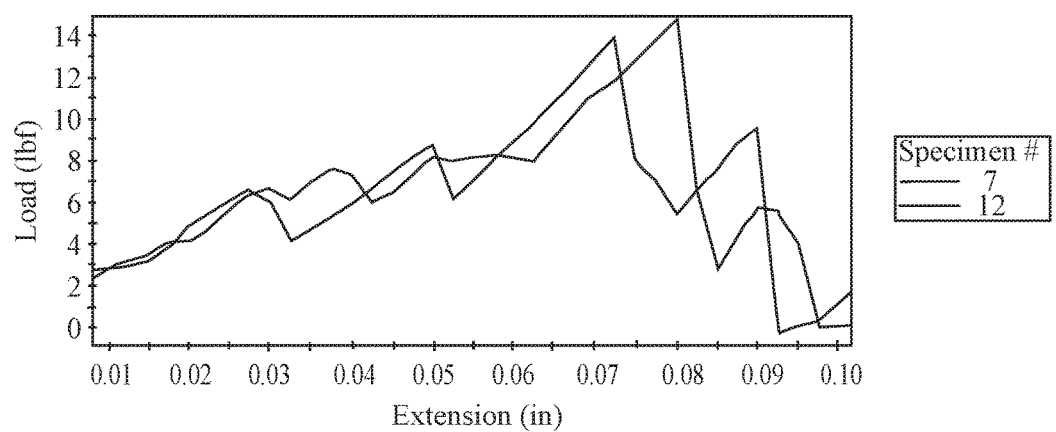
FIG. 15 is a graph of the load required to the deform the cinch on the suture.

The movement of the handle 102 from the second position to the third position at which complete deformation of the ribs and cutter tab 42 displacement occurs preferably is a continuous process. FIG. 15 illustrates load on the shaft 110 as the ribs 34 are deformed in sequence. It is noted that the load increases as each subsequent rib is deformed. The system is designed to require a load of less than 15 lb-f to deform the ribs and move the cutter tab 42 to cut the suture, and subject the shaft to a tensile extension of less than 0.08 inches at such maximum load. Less preferably the system can be required to operate with greater loads; however, such may require use of stronger shaft materials and can be more difficult to manually operate to deform the cinch and cut the suture.

Figure 16:
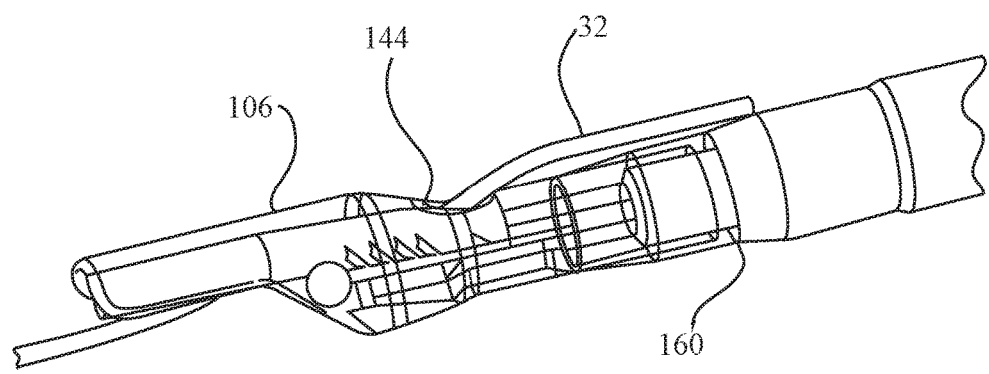
FIGS. 16 and 17 are broken distal end perspective views illustrating a cutting feature of the cinch applicator.
Figure 17:
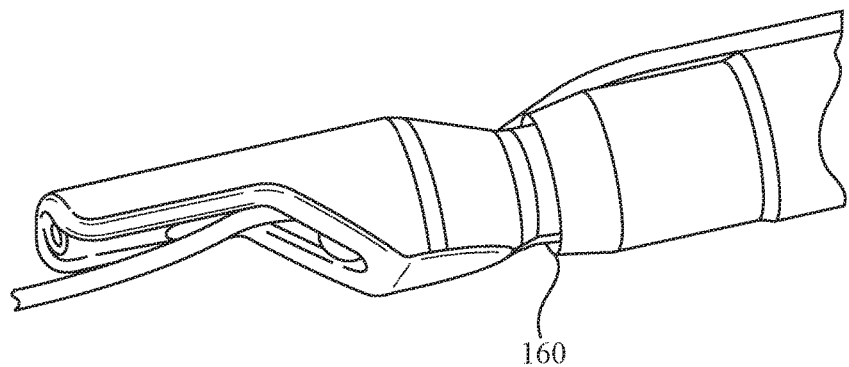

Turning now to FIG. 16, in accord with another aspect of the invention, in an embodiment in which the cinch 10a does not define an integrated cutter, the cinch applicator is provided with suitable cutter 160 to cut the suture 32 after the cinch is secured on the suture. By way of example only, such cutter 32 is one that can be moved relative to the window 144 in the housing 106 in a longitudinal or rotational manner, or a punch that is sufficiently movable through the window to sever the suture extending through the window from the suture attached to the cinch and tissue. In the example shown in FIG. 17, the cutter 160 is longitudinal displaceable across the window 144 to cut the suture. Such displacement is actuated by operation of the handle 102.

With reference to the following description of the cinch loader 200, the terms "proximal" and "distal" are defined with respect to the loader being located in a coupled relationship at the distal end of the applicator, where it is used to load a suture cinch into the applicator, as now described. The use of the loader is particularly advantageous, as the cinch is particularly small, thereby rendering it somewhat impractical for manipulation into the proper orientation into the housing solely by the fingers of an operator. The loader can be provided preloaded with a cinch or can be operator-loaded with a cinch from a store of cinches for subsequent loading of the cinch into the applicator.

Figure 18:
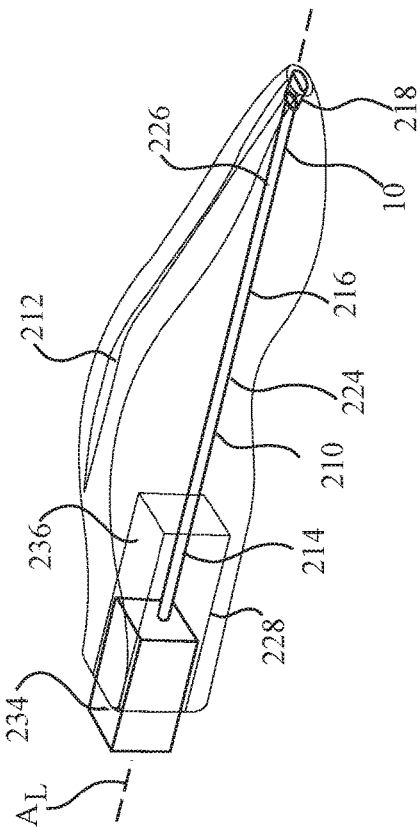
FIG. 18 is a perspective view of a cinch loader.
Figure 19:
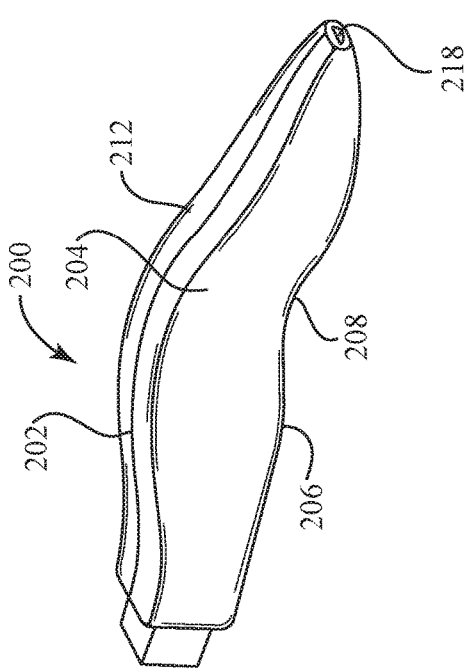
FIG. 19 is a transparent perspective view of the cinch loader of FIG. 18.

Referring now to FIGS. 18 and 19, the loader 200 includes a body 202 preferably having a convexly arced upper surface 204 and defining a lower surface 206 with a recess 208 for a finger holed. The shape is well-adapted for comfortable and stable handling by the operator. The body 202 defines a straight throughbore 210 defining a longitudinal axis $A_L$ that extends through the body, and a suture guide slot 212. The throughbore 210 has distal (first), central, and proximal (second) portions, respectively 214, 216, 218. The distal portion 214 of the throughbore 210 has a non-circular and preferably square cross-sectional shape in a direction transverse to the longitudinal axis $A_L$. The central portion 216 is relatively smaller in diameter and preferably has a circular cross-sectional shape transverse to the longitudinal axis $A_L$. The proximal portion 218 has a shape and size corresponding to the distal end of the housing 106 of the applicator 100 and particularly the hood 130 thereof so that the hood may be stably inserted and retained therein (see FIG. 9). To that end, the proximal portion 218 has a concavely curved wall 220 and an opposed flat wall 222. The suture guide slot 212 extends along the exterior upper surface 204 of the body 202 and leads into the proximal portion 218 of said throughbore interrupting the flat wall 222. The guide slot 212 is an open structure.

Figure 20:
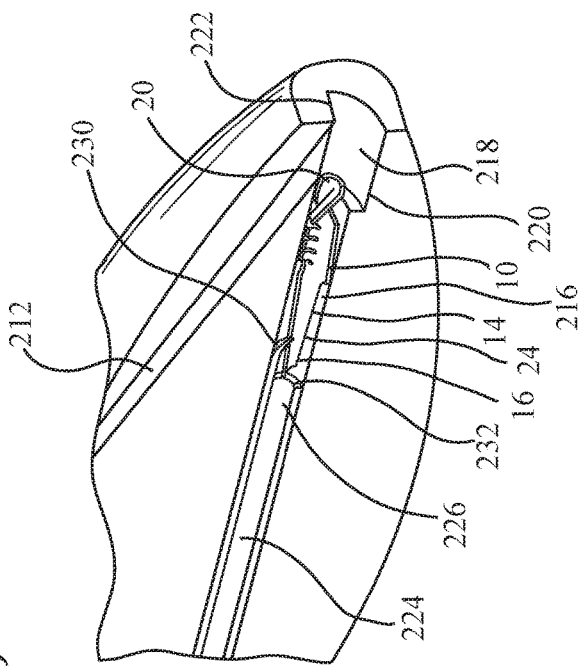
FIG. 20 is a broken longitudinal section view of the proximal end of the cinch loader.

Referring to FIGS. 19 and 20, a cinch pusher 224 and a cinch 10 are longitudinally displaceable within the central portion 216 of the throughbore. The cinch pusher 224 has a proximal end 226 and distal end 228. The proximal end 226 of the pusher defines a first tip portion 230 provided with a shape, e.g., a hook, such that it engages the lateral entry opening 22 in the cinch 10 to retain the cinch within the central portion 216 of the throughbore 210 under tension, and a second tip portion 232 that butts against the first end 16 of the cinch and having a shape suitable for applying a pushing force thereagainst under compression, e.g., an orthogonal face. In a cinch-loaded configuration, with the lateral entry 22 opening of the cinch engaged by the first tip portion 230, the second end 20 of the cinch (e.g., from and proximal the exit opening of the cinch) extends into the proximal portion 218 of the throughbore to facilitate loading the cinch into the housing 106 of the applicator, as described below. Further, the engagement of by the first tip portion 230 cants the cinch 10 onto the first side 24 of the first portion 14 thereof to raise the second end 20 of the cinch to also facilitate loading the cinch onto the hood 130 and into the socket 132 of the applicator 100.

A button 234 is displaceable within the distal portion 214 of the throughbore and is rotationally fixed to the distal end 228 of the pusher 224. The button 234 is provided with a shape that rotationally interferes with the distal portion 214 of the throughbore; this limits rotation of the first tip portion 230 of the pusher and thus stabilizes the orientation of the cinch 10. The button 234 may assume the shape of a rectangular solid or another suitable shape, and the shape thereof may be dependent on the shape of the distal portion 214 of the throughbore 210. Other means may be used to limit rotation of the pusher and/or the cinch. The button 234, in an initial position, extends partially out of the distal portion 214 of the throughbore so that it can be contacted and displaced proximally by a finger of an operator.

Turning to FIG. 21, the hood 130 of the housing 106 is received into the proximal portion 218 of the throughbore 210 such that once fully inserted, the cinch 10 is aligned for advancement into the hood 130 and the socket 132. Referring to FIG. 22, then, the button 234 is pushed relative to the body 202 causing the second tip portion 232 to advance the cinch 10 into the hood 130 and socket 132, with the entry opening 22 of the cinch facing the open side of the hood 130 and the exit opening 26 of the cinch 10 aligning with the window 144 of the housing 106. The extent of longitudinal displacement of the button 234, and thus the displacement of the cinch 10, is limited; the button bottoms out against a shoulder 236 defined by the transition between the distal and central portions 214, 216 of the throughbore (FIG. 19).

Turning now to FIG. 23, once the loader 200 is operated to advance the cinch 10 longitudinally into and in proper alignment with the housing 106, the suture guide slot 212 is utilized to facilitate feeding the suture 32 into the entry opening 22, through the pathway 30, and out of the exit opening 26 of the cinch, as well as out of the window 144 of the housing. (See FIGS. 10 and 22 for details of the described pathway) As shown in FIG. 24, after the suture 32 has been fed through the intended pathway in the cinch and housing, the open structure of the slot 212 allows the suture 32 to be pulled away from the loader 200, or the loader to be uncoupled from the applicator 100 and the loader to be pulled away from the suture 32.

In use, the handle 102 of the applicator 100 is operated to advance the bead 126 at the distal end of the shaft 110 to a location sufficient distal of the socket to permit loading of a cinch. The hood 130 is then advanced into a cinch-loaded loader 200, button 234 of the loader is operated to load the cinch 10 into the housing 106, the handle 102 of the applicator is operated to retract the bead 126 proximally to engage and restrain the cinch relative to the housing, and the suture 132 is fed through the cinch 10 and out of the window 144 of the housing. The loader 200 is then uncoupled from the housing 106 of the applicator 100.

The described system has particular use in endoscopic procedures, in a natural orifice procedure in which an endoscopic stitching instrument has applied one or more stitches of suture through tissue, in a procedure on gastrointestinal tissue where it is necessary or desirable to secure one or more sutures, or in any other endoscopic procedure where it is necessary or desirable to secure one or more sutures. In a mode of such stitching, a needle fixed to one of the suture is advanced through the tissue and carries the suture through the tissue. Once the tissue is sufficiently stitched to approximate the tissue, the cinch applicator loaded with a cinch, in accord with the above, is provided for cinching the suture against the tissue and/or relative to the suture needle. Subsequently, the cinch applicator may be withdrawn from the patient, a new cinch may be loaded into the cinch housing, preferably through use of the cinch loader, and the cinch applicator can be used again to secure an addition suture. The process may be repeated as necessary.

There have been described and illustrated herein embodiments of a cinch applicator and a method of applying a cinch. While particular embodiments of the invention have been described, it is not intended that the invention be limited thereto, as it is intended that the invention be as broad in scope as the art will allow and that the specification be read likewise. Thus, while particular dimensions have been described for the cinch and angles have been described with respect to portions of the cinch applicator, it will be appreciated that other suitable dimensions and angles for the components can be used as well. Also, while preferred materials are described, it is appreciated that other materials can be used. In addition, while the applicator has been described with respect to a flexible tubular member and shaft, which make the applicator ideally suited for insertion through the working channel of an endoscope that can be bent through an arc of up to 180°, the applicator alternatively may be assembled with a rigid tubular member and flexible or rigid shaft rendering the applicator more suitable for laparoscopic or open surgery. In each of such laparoscopic and open uses, the cinch can be of an appropriately larger size. It will therefore be appreciated by those skilled in the art that yet other modifications could be made to the provided invention without deviating from its scope as claimed.

What is claimed is:

1. A cinch for a cinch applicator for securing suture to a tissue, the cinch applicator having a tubular member with a distal housing in which the cinch can be seated, and a shaft displaceable relative to the tubular member and having a force-applying member at its distal end, said cinch consisting of:
a unitary tubular element defining a longitudinal axis, a first longitudinal portion defining a first end of said tubular element, a second longitudinal portion opposite said first longitudinal portion and defining a second end of said tubular element, a periphery having a first hemi-tubular portion and an opposite second hemi-tubular portion, an entry opening in the first hemi-tubular portion to a first side of the longitudinal axis and at said first portion, an exit opening in the second hemi-tubular portion to an opposite second side of the longitudinal axis, said entry and exit openings facing in opposite directions, a suture pathway defined from said entry opening and through said exit opening, at least one plastically deformable rib defined in said second longitudinal portion and extending at least partially about said first hemi-tubular portion transverse to said longitudinal axis, and a seat adapted to receive a portion of said force-applying member in said first hemi-tubular portion between said entry opening and said at least one deformable rib,
wherein when the suture is extending through said entry opening, said pathway, and out of said exit opening, and
when said force-applying member is forcibly retracted from said seat and into contact with said at least one rib, said at least one rib is adapted to plastically deform to secure said suture within said pathway.

2. A cinch according to claim 1, wherein:
said periphery is round.

3. A cinch according to claim 1, wherein:
said at least one rib is a plurality of ribs, and said ribs are configured to be plastically deformed in sequence upon being subject to a longitudinal deformation force along an exterior of said periphery at said second longitudinal portion in a direction from said first end to said second end.

4. A cinch according to claim 3, wherein:
said ribs are obliquely oriented relative to the longitudinal axis.

5. A cinch according to claim 4, wherein:
said ribs are defined by laser cut slots about said periphery of said tubular element.

6. A cinch according to claim 4, wherein:
said ribs each have a leading end oriented toward said first end of said tubular member, and a trailing end oriented toward said second end of said tubular member, and said leading end is defined by a curvilinear surface and said trailing end is defined by straight surfaces.

7. A cinch according to claim 1, wherein:
said first longitudinal portion at said second hemi-tubular portion of said periphery includes an exterior surface oriented obliquely relative to said longitudinal axis and extending to the first end.

8. A cinch according to claim 1, wherein:
said entry opening is elongate, having a first edge nearer said first end and a second edge nearer said second end.

9. A cinch according to claim 8, wherein:
said second hemi-tubular portion at said first longitudinal portion is provided with an exterior surface oriented obliquely relative to said longitudinal axis, and said exterior surface extends from said first end to proximate said second edge of said entry opening.

10. A cinch according to claim 1, wherein:
said tubular element includes an integral tab extending into said pathway to deflect said suture from said pathway toward said exit opening.

11. A cinch according to claim 1, wherein:
said tubular element includes an integral tab extending from said second hemi-tubular portion and into said pathway, said tab adapted to be plastically deformed toward said exit opening and cut the suture passing through said exit opening when the force-applying member is forcibly retracted past said at least one rib and into contact with said tab.

12. A cinch according to claim 1, wherein:
said tubular element is metal.

13. A cinch according to claim 1, wherein:
said tubular element is a portion of a hypotube.

14. A cinch according to claim 1, wherein:
said tubular element has a length not exceeding 15 mm and diameter not exceeding 1.5 mm.

15. A cinch for a cinch applicator for securing suture to a tissue, the cinch applicator having a tubular member with a distal housing in which the cinch can be seated, and a shaft displaceable relative to the tubular member and having a force-applying member at its distal end, said cinch consisting of:
a unitary tubular element defining a longitudinal axis, a first longitudinal portion defining a first end of said tubular element, a second longitudinal portion opposite said first longitudinal portion and defining a second end of said tubular element, a periphery having a first hemi-tubular portion and an opposite second hemi-tubular portion, an entry opening in the first hemi-tubular portion to a first side of the longitudinal axis and at said first portion, an exit opening in the second hemi-tubular portion to an opposite second side of the longitudinal axis, said entry and exit openings facing in opposite directions, a suture pathway defined from said entry opening and through said exit opening, at least one plastically deformable rib defined in said second longitudinal portion and extending at least partially about said first hemi-tubular portion transverse to said longitudinal axis,
a tab extending from said second hemi-tubular portion at said second longitudinal portion of said tubular element and into said pathway,
wherein when the suture is extending through said entry opening, said pathway, and out of said exit opening and when the force-applying member is forcibly retracted into contact with said at least one rib, said at least one rib is adapted to plastically deform to secure the suture within said pathway, and said tab is adapted to be moved toward said exit opening and cut the suture passing through said exit opening.

16. A cinch according to claim 15, wherein:
said first hemi-tubular portion at said second longitudinal portion includes an integral seat between said entry opening and said at least one deformable rib, said seat adapted to receive a portion of said force-applying member.

17. A cinch for a cinch applicator for securing suture to a tissue, the cinch applicator having a tubular member with a distal housing in which the cinch can be seated, and a shaft displaceable relative to the tubular member and having a force-applying member at its distal end, said cinch comprising of:
a unitary tubular element defining a longitudinal axis, a first longitudinal portion defining a first end of said tubular element, a second longitudinal portion opposite said first longitudinal portion and defining a second end of said tubular element, a periphery having a first hemi-tubular portion and an opposite second hemi-tubular portion, an entry opening in the first hemi-tubular portion to a first side of the longitudinal axis and at said first portion, an exit opening in the second hemi-tubular portion to an opposite second side of the longitudinal axis, said entry and exit openings facing in opposite directions, a suture pathway defined from said entry opening and through said exit opening, at least one plastically deformable rib defined in said second longitudinal portion and extending at least partially about said first hemi-tubular portion transverse to said longitudinal axis,
a tab integral with said tubular element and extending into said pathway to deflect said suture from said pathway toward said exit opening,
wherein when said suture is extending through said entry opening, said pathway, and out of said exit opening and when the force-applying member is forcibly retracted into contact with said at least one rib, said at least one rib is adapted to plastically deform to secure said suture within said pathway, and at least one of said at least one rib is further adapted to contact said tab and displace said tab to cause said tab to sever said suture exiting through said exit opening.

18. A cinch according to claim 17, wherein:
said first hemi-tubular portion at said second longitudinal portion includes an integral seat between said entry opening and said at least one deformable rib, said seat adapted to receive a portion of said force-applying member.

19. A cinch for a cinch applicator for securing suture to a tissue, the cinch applicator having a tubular member with a distal housing in which the cinch can be seated, and a shaft displaceable relative to the tubular member and having a force-applying member at its distal end, said cinch comprising:
a unitary tubular element defining a longitudinal axis, a first longitudinal portion defining a first end of said tubular element, a second longitudinal portion opposite said first longitudinal portion and defining a second end of said tubular element, a periphery having a first hemi-tubular portion and an opposite second hemi-tubular portion, an entry opening in the first hemi-tubular portion to a first side of the longitudinal axis and at said first portion, an exit opening in the second hemi-tubular portion to an opposite second side of the longitudinal axis, said entry and exit openings facing in opposite directions, a suture pathway defined from said entry opening and through said exit opening, at least one plastically deformable rib defined in said second longitudinal portion and extending at least partially about said first hemi-tubular portion transverse to said longitudinal axis,
- wherein when said suture is extending through said entry opening, said pathway, and out of said exit opening, and
- when said force-applying member is forcibly retracted into contact with said ribs, said ribs are adapted to plastically deform to secure said suture within said pathway.

20. A cinch according to claim 19, wherein:
said first hemi-tubular portion at said second longitudinal portion includes an integral seat between said entry opening and said at least one deformable rib, said seat adapted to receive a portion of said force-applying member.

\* \* \* \* \*